US006926888B1

(12) United States Patent
Bjerkvig (10) Patent No.: US 6,926,888 B1
(45) Date of Patent: Aug. 9, 2005

(54) ALGINATE CAPSULES FOR USE IN THE TREATMENT OF BRAIN TUMOR

(75) Inventor: Rolf Bjerkvig, Mathopen (NO)

(73) Assignee: FMC Biopolymer AS, Drammen (NO)

(*) Notice: Subject to any disclaimer, the term of this patent is extended or adjusted under 35 U.S.C. 154(b) by 0 days.

(21) Appl. No.: 09/763,682

(22) PCT Filed: Aug. 25, 1999

(86) PCT No.: PCT/NO99/00266

§ 371 (c)(1),
(2), (4) Date: Apr. 27, 2001

(87) PCT Pub. No.: WO00/12066

PCT Pub. Date: Mar. 9, 2000

(30) Foreign Application Priority Data

Aug. 26, 1998 (NO) .......................................... 19983911

(51) Int. Cl.[7] .............................................. A61K 48/00
(52) U.S. Cl. .................. 424/93.2; 424/93.21; 424/424; 435/178; 435/182; 435/325; 435/375
(58) Field of Search ............................. 424/93.2, 93.21, 424/424; 435/178, 182, 325, 375; 514/44

(56) References Cited

U.S. PATENT DOCUMENTS

| 5,166,137 A | 11/1992 | Otterlei et al. ................. 514/23 |
| 5,459,054 A | * 10/1995 | Skjak-Braek et al. ....... 435/178 |
| 5,854,205 A | * 12/1998 | O'Reilly et al. ............... 514/2 |

FOREIGN PATENT DOCUMENTS

| WO | 92/19195 | 11/1992 |
| WO | 96/01611 | 1/1996 |
| WO | 96/28029 | 9/1996 |
| WO | 97/36495 | 10/1997 |
| WO | 97/38707 | 10/1997 |
| WO | 97/44065 | 11/1997 |

OTHER PUBLICATIONS

T Visted et al., Neuro–Oncology, "Cell encapsulation technology as a therapeutic strategy for CNS malignancies," Jul. 2001, pp. 201–210.*
MS O'Reilly et al.,Cell,"Endostatin:An Endogenous Inhibtor of Angiogenesis and Tumor Growth," Jan. 1997, vol. 88, pp. 277–285.*
Skjåk–Braek and Espevik, "Application of alginate gels in biotechnology and biomedicine," *Carbohydrates in Europe*, vol. 14, pp. 19–25, 1996.
Kulseng et al., "Alginate polylysine microcapsules as immune barrier: Permeability of cytokines and immunoglobulins over the capsule membrane," *Cell Transplantation*, vol. 6, pp. 387–394, 1997.
Smidsrød and Draget, "Chemistry and physical properties of alginate," *Carbohydrates in Europe*, 14, 6–13, 1996.

Read, T.–A. et al., "Cells Encapsulated in Alginate: A Potential System for Delivery of Recombinant Proteins to Malignant Brain Tumours," Int. J. Dev. Neuroscience, vol. 17, No. 5–6, pp. 653–663, 1999.
Lund, E.L. et al., "Tumor Angiogenesis—A New Therapeutic Target in Gliomas," Acta Neurol. Scand., vol. 97, No. 1, pp. 52–62, 1998. (Abstract only).
Yin, D.X. et al., "Tetracycline–controlled Gene Expression System Achieves High–lev I and Quantitative Control of Gene Expression," Anal. Biochem., vol. 235, No. 2, pp. 195–201, 1996. (Abstract only).
Otterlei, M. et al., "Induction of Cytokine Production From Human Monocytes Stimulated With Alginate," J. Immunother., vol. 10, No. 4, p. 286–291. (Abstract only).
Avalosse, B. et al., "Gene Therapy for Cancer", Curr. Opin. Oncol., vol. 7, pp. 94–100, 1995.
Gordon, Erlinda M. et al., "Gene Therapy Using Retroviral Vectors", Curr. Opin. Biotechnol, vol. 5, pp. 611–616, 1994.
Steele, Cherrilee et al., "Effects of Human Papillomavirus Type 18–specific Antisense Oligonucleotides on the Transformed Phenotype of Human Carcinoma Cell Lines", Cancer Res., vol. 53, No. 10 pp. 2330–2337, 1993.
Zhang, Y. et al., "Retroviral Vector–Mediated Transduction of K–ras Antisense RNA into Human Lung Cancer Cells Inhibits Expression of the Malignant Phenotype", Hum. Gen Ther., vol. 4, pp. 451–460, 1993.
Tepper, Robert I. et al., "Experimental and Clinical Studies of Cytokine Gene–Modified Tumor Cells", Hum. Gene Ther., vol. 5, pp. 153–164, 1994.
Pardoll, Drew M., "Cancer Vaccines", Trends Pharmacol. Sci., vol. 14, pp. 202–208, 1993.
Smidsrød and Skjak–Braek, "Alginate as Immobilization Matrix for Cells," Trends in Biotechnology, vol. 8, pp. 71–78, 1990.
Laerum, O.D. et al., "Neoplastic Transformation of Fetal Rat Brain Cells in Culture Aft r Exposure to Ethylnitrosourea In Vivo", J. Natl. Cancer Inst., vol. 55, No. 5, pp. 1177–1187, 1975.
Thorsen, F. et al., "Release of Replication–Deficient Retroviruses From a Packaging Cell Line: Interaction with Glioma Tumor Spheroids in Vitro", Intl. J. Cancer, vol. 71, No. 5, pp. 874–880, 1997.
Anderson, M.L.M. et al., "Onco–Suppressor Genes and Their Involvement in Cancer", Anticancer Research, vol. 8, No. 5A, pp. 873–879, 1988.

(Continued)

*Primary Examiner*—Dave Trong Nguyen
*Assistant Examiner*—Jon Eric Angell
(74) *Attorney, Agent, or Firm*—Woodcock Washburn LLP (57) ABSTRACT

Encapsulated producer cells which are capable of expressing a molecule which is an inhibitor of CNS tumour growth provide a novel approach to the treatment of tumours, such as brain tumors which are localized within the central nervous system.

15 Claims, 7 Drawing Sheets

OTHER PUBLICATIONS

Kim et al., "Specific Association of Human Telomerase Activity with Immortal Cells and Cancer", Science, vol. 266, pp. 2011–2015, 1994.

Lund–Johansen, M. et al., "Effects of Growth Factors on a Human Glioma Cell Line During Invasion Into Rat Brain Aggregates in Cultur", Acta Neuropathol., vol. 84, No. 2, pp. 190–197, 1992.

Baisch, H. et al., "Analysis of PCP–Data to Determine the Fraction of Cells in the Various Phases of Cell Cycle", Radiat. Environ. Biophys., vol. 12, No. 1, pp. 31–39, 1975.

Soon–Shiong, P. et al., "Successful Reversal of Spontaneous Diabetes in Dogs by Intraperitoneal Microencapsulated Islets", Transplantation, vol. 54, No. 5, pp. 769–774, 1992.

* cited by examiner

ALGINATE CAPSULES FOR USE IN THE TREATMENT OF BRAIN TUMOR

This invention is in the field of the treatment of tumours which are localized within the central nervous system (CNS) and of primary and secondary (metastatic) cerebral-spinal malignancies, and it provides new compositions and delivery systems useful in such therapy.

Primary brain tumours (gliomas) have several unique biological features compared to other metastatic tumours. They are confined within the central nervous system and metastatic spread to other organs is virtually non-existent. Even though these tumours show a high degree of invasion into the brain they have a tendency to recur after treatment in positions where they originally were found. The tumours are highly heterogeneous and consist of numerous cell types with different phenotypic properties.

At present the treatment of choice is surgery followed by radiotherapy and chemotherapy. Patients with the most malignant forms of brain tumours (glioblastomas) have a severe prognosis with a survival of approximately 10 months after diagnosis. There is therefore an urgent need for new treatment strategies for this particular group of tumours. Since the tumours have a tendency to recur at its primary site, new local treatment strategies are needed. Furthermore since these tumours consist of numerous tumour cells with different phenotypic properties, the treatment of choice should be capable of targeting different tumour cell types.

Other tumours which are localized within the central nervous system and which are often difficult to treat successfully include tumours derived from astroglial and oligodendroglial cells, for instance:

Astrocytomas
  Low grade astrocytomas (astrocytomas grade 1 and 2)
  Anaplastic astrocytoma (astrocytoma grade 3)
  Glioblastoma multiforme (astrocytoma grade 4)
    including secondary glioblastoma, i.e. tumours that have differentiated from astrocytomas with lower grade
    primary glioblastoma, i.e. tumours that occur as primary glioblastomas de novo
    giant cell glioblastoma
    gliosarcomas
    gliomatosis cerebri
Oligodendrogliomas
  including oligodendroglioma (WHO grade II)
  anaplastic oligodendroglioma (WHO grade III)
Mixed Gliomas
  Oligoastrocytoma (WHO grade II)
  Anaplastic oligoastrocytoma (WHO grade III)
Ependymal Tumours
  Ependymoma (WHO grade II)
  Anaplastic ependymoma (WHO grade III)
  Subependymoma (WHO grade I)
Embryonal Tumours
  Central neuroblastoma
  Ependymoblastoma
  Medulloblastomas
  Supratentorial PNETs
Neuroblastomas
  Olfactory neuroblastoma
  Neuroblastic tumours of the adrenal gland and sympathetic nervous system For most of these tumours, the first treatment of choice is surgery followed with radiotherapy and/or with chemotherapy. However, complete tumour removal is often difficult by surgical procedures, whilst follow-up radiotherapy and chemotherapy are also sometimes not completely successful due to radioresistance and/or difficulties in delivering therapeutic doses of cytotoxic drugs.

During recent years much attention has been focused on gene therapy, where reversion of the malignant phenotype by downregulation of oncogene expression or insertion of normal tumour-suppressor genes have been tried. Immune stimulatory factors such as cytokines that are designed to enhance the recognition and rejection of tumours by the immune system have also been introduced. Furthermore, cells have been modified to allow direct delivery of gene products to tumour cells, increasing their susceptibility to pharmacological agents. Papers which describe these developments include (i) Curr Opin Oncol, 7, (1995), pages 94–100; (ii) Curr Opin Biotechnol, 5, (1993), pages 2330–7; (iv) Hum Gene Ther, 4, (1993), pages 451–60; (v) Hum Gene Ther, 4, (1994), pages 153–164; and (vi) Trends Pharmacol. Sci, 14, (1993), pages 202_208.

Despite this extensive research during recent years, there are major obstacles which impede the transition between experimental research and clinical treatment of malignant brain tumours. One problem is to prevent immuno-rejection of genetically modified cells after intracranial implantation. This may be overcome by encapsulating the producer cells.

However, this results in other problems, to find materials especially adapted for use in the brain. Although, the brain is immunologically different from other areas of the body, for instance in its lack of B lymphocytes, it is especially sensitive to the influence of biologically active compounds such as for instance endotoxins.

We have now found, in accordance with the present invention, that immuno-isolating alginate matrices are especially suitable for the encapsulation of producer cells intended for implantation intercranially, in the treatment of CNS tumours. It is especially preferred that the immuno-isolating alginate matrices should be microbeads.

Thus, in its broad aspect, the present invention provides an encapsulated producer cell capable of expressing a molecule which is an inhibitor of CNS tumour growth, which producer cell is encapsulated in an immuno-isolating alginate matrix. It is preferred that this molecule should be a peptide, a protein or a polysaccharide and most preferred the molecule is a monoclonal antibody.

The present invention also provides a method for the treatment of CNS tumours, which comprises implanting at the site of the tumour an encapsulated producer cell which is capable of expressing a molecule which is an inhibitor of the growth of said tumour.

Further, the present invention provides a method for the preparation a pharmacological product for the treatment of a CNS tumour, which comprises encapsulating within an immuno-isolating alginate matrix a producer cell capable of expressing a molecule which is an inhibitor of the growth of said tumour.

The present invention also provides for the use of immuno-isolating alginate matrices for encapsulation of producer cells intended for implantation intercranially, in the treatment of CNS tumours.

In one embodiment of the invention the producer cells contemplated for use herein include genetically engineered cells that produce molecules e.g. proteins, peptides and polysaccharides, that will either directly interact with tumour cells or indirectly with tumour or host cell communication pathways. Other useful producer cells contemplated herein are specialized cells which produce monoclonal antibodies as for instance hybridoma cells, or even naturally occurring cells capable of expressing tumour inhibiting molecules.

It is well known that tumour growth is dependent on specific cellular interactions with the host, mediated via specific growth factors that regulate tumour cell growth in rather complex ways. The tumours depend in this respect on nutrients mediated via newly formed blood vessels supplied by the host. Several tumour/host cellular interaction pathways have during the last years been identified and described in the literature.

Accordingly, one class of producer cell useful herein are those which can express proteins or peptides that will interact with tumour/host communication pathways. For instance, useful producer cells include those which produce proteins and peptides which affect tumour neovascularization as for instance thrombospondin, endostatin, angiostatin and prolactin, proteins which interfere with the tumour cells' relationship to the extracellular matrix, for instance protease inhibitors such as tissue inhibitors of metalloproteinases, and proteins and peptides which affect the immune system, including all the various classes of interleukins.

Another preferred class of producer cell is constituted by those which express proteins or peptides which interact directly with the tumour cells themselves. For instance, useful producer cells of this category include: hybridoma cell lines that produce monoclonal antibodies which interact directly with a receptor of the tumour, for example cell growth factor receptors which affect the tumour cells such as epidermal growth factor receptor (EGFr), platelet derived growth factor receptors AA and BB; acidic and basic fibroblast growth factor receptors, transforming growth factor receptor alpha and beta, the different classes of vascular endothelial growth factor receptors (VEGFR-1 and VEGFR-2), tyrosine kinase receptors with immunoglobulin and EGF-like domains as, for instance, TIE-1 and TIE-2/tek, heptaocyte growth factor (scatter factor); or monoclonal antibodies directed against various classes of integrin receptors; monoclonal antibodies directed against CD-44; monoclonal antibodies directed against CDK/cyclin complexes; monoclonal antibodies directed against FAS; monoclonal antibodies directed against glycolipids on the cell surface; monoclonal antibodies directed against glycoproteins; and monoclonal antibodies directed against proteins derived from the expression of specific oncogenes.

Of particular interest in some circumstances are producer cells whose production of tumour growth-inhibiting substances can be switched on and off by pharmacological means, for instance producer cells with pharmacologically-inducible gene expression as, for example, tetracycline-activated gene expression.

Any cell line which is transfectable may be used in accordance with this invention. The cell lines should be permanent, i.e. able to undergo unlimited cell division, and preferably are non-human and non-tumorigenic.

Examples of such cell lines which are freely commercially available from the American Type Culture Collection, 10350 Linden Lake Plaza, Manassas, Va. 20109, USA, are:

| Cell Line | ATCC number | Description |
| --- | --- | --- |
| H528 | HB 8509 | mouse B cell myeloma |
| 293 | CRL 1573 | human transformed primary embryonal kidney |
| NIH/3T3 | CRL 1658 | NIH swiss mouse, embryo |
| COS-7 | CRL 1651 | African green monkey, kidney, SV40 transform |
| BHK-21 | CCL 10 | Hamster kidney, normal |
| CV-1 | CCL 70 | African green monkey, kidney, normal |
| CHP-234 | CRL-2272 | Neuroblastoma, brain, human |
| Rat2 | CRL-1764 | Embryo, thymidine kinase mutant, rat |
| Namalwa | CL-1432 | Burkitt's lymphoma, human |

In accordance with the present invention, the producer cells are encapsulated in immuno-isolating alginate matrices which are capable of providing a stable, in situ delivery system of expressed protein or other molecule which can interfere with tumour growth and progression without immuno-rejection of the producer cells.

The encapsulation of cells within alginate beads is a well known technique for immobilising cells and other substances, and has previously been used in the treatment of diabetes mellitus, in the production of monoclonal antibodies, and in other medical areas, as has been described in the literature.

From PCT/WO97/44065 this present drug delivery technique has been proposed for in vivo gene therapy using encapsulated cells releasing gene transfer vectors at the site of a brain tumour. The capsules used for encapsulating the cells comprise two parts: a) a core comprising living packaging cells and b) an external jacket surrounding said core.

The present invention provides for a much simpler encapsulation process and product, wherein the producer cells are encapsulated directly in a one-step procedure using an immuno-isolating alginate quality.

Alginate is a polysaccharide which is mainly found in brown seaweed. It consists of two types of monosaccharides; L-guluronic acid (G) and D-mannuronic acid (M). These polysaccharide units appear in blocks of alternating sequences of G and M (MG-blocks) and blocks mainly consisting of either G or M units (G-blocks/M-blocks).

The gelforming property is achieved through a cross-link of G-blocks with multivalent cations, especially $Ca^{2+}$.

In order for an alginate not to be immunogically activating the G content must be above 15%. However it is more preferred, according to the present invention to use a high G alginate, i.e. with a G content of 50% or more in order to acertain that the alginate is immuno-isolating. As is well-known in the art the G/M-block ratios and the distribution of the different blocks are critical factors for the different properties of the resulting gel formed through cross-linking with a polyvalent cation.

Another aspect which is critical is the purity of the alginate to be used. Thus, one advantage of the alginate matrices usable according to the present invention is that they may be produced in a high-purity quality having a well defined constitution and a very low content of impurities such as endotoxins.

A second advantage of the alginate matrices usable according to the present invention is that alginate microbeads prepared by the drop-wise addition of an alginate solution containing viable cells to a calsium solution, have a rising alginate concentration from the center of the microbead to the outer rim. Thereby an optimal space is created at the center of the microbeads for the cells to live, profilate and produce whereby sufficient nutrients and oxygen is available to the cells. The outer rim with its higher alginate concentration gives rise to a barrier, so that the producing cells inside the microbeads do not escape from the interior, nor do immunological cells enter into the beads.

Generally, the use of alginate as an immobilisation matrix for cells involves mixing a suspension of the cells with a $Na^+$ alginate solution, whereafter the mixture is dripped into a solution containing multivalent cations (usually $Ca^{2+}$). The droplets form gel spheres instantaneously entrapping the cells in a three-dimensional lattice of ionically crosslinked alginate. This immobilisation procedure can be carried out under very mild conditions and is therefore compatible with most living cells. For a detailed description both of the theory and practice of the technique, the reader is directed to the paper "Alginate as Immobilization Matrix for Cells" by Smidsrød and Skjak-Braek in Trends in Biotechnology, March 1990, Vol. 8, No. 3, pages 71–78.

A currently preferred method for forming producer cell-encapsulated calcium alginate beads in accordance with this invention is as follows. Sodium alginate is dissolved at a concentration of from 1–2% in water or isotonic saline. The alginate solution is membrane sterilized, and the producer cells are then added and isotonicity adjusted. Calcium alginate beads are formed by dripping the sodium alginate-producer cell solution into a bath of calcium chloride (0.05–0.25 M), either manually but preferably using an electrostatic bead generator which establishes an electrostatic potential of 5 to 7 kV between the alginate feed needle and the gelling bath. By adjusting the needle diameter (e.g. from 0.1 mm to 0.4 mm), the flow rate (e.g. from 5 ml/hr to 30 ml/hr) and the voltage applied, beads of comparatively uniform diameter of from 100–400 µm can be generated. The homogeneity of the beads is controlled by adjusting the salt concentration in the gelling bath, from 0 to 200 mM NaCl, with the higher salt concentration giving greater homogeneity. The beads are allowed to harden in the gelling bath.

It is contemplated that the encapsulated producer cells of this invention will be placed into the tumour cavity following conventional bulk tumour removal by surgery. Shortly after surgery the tumour burden is minimal and many patients have a symptom-free period before recurrence occurs. Since surgery is a traumatic event, the remaining tumour cells will try to establish new biochemical interaction pathways with the host. This involves the formation of new blood vessels and new supplies of peptide growth factors to the remaining tumour cells. It is at this time, when the tumour burden is at a minimum, that the treatment made possible by the present invention is most likely to be effective.

It is, indeed, a particular advantage of the present invention in accordance with one embodiment that it readily permits the simultaneous implantation of several different types of producer cells to target different phenotypic characteristics and microenvironmental factors influencing the progressive growth of brain or other tumours. For this purpose, a producer cell bank containing encapsulated producer cells stored frozen at the temperature of liquid nitrogen could be established. Producer cells could then be withdrawn from the bank to meet the genotypic expression of the host tumour being treated.

In order to establish what producer cells are required for treatment of a tumour the following procedure could be used, by way of example. Tumour characterization involving determination of receptor status and phenotype is first performed on biopsy material. Appropriately chosen producer cells which produce substances, for example monoclonal antibodies, directed against the receptor status of the host tumour is then implanted stereotactically up to 60 days following surgical removal of the primary tumour.

Alternatively, producer cells producing anti-angiogenic substances can be implanted directly following surgical removal of the primary tumour.

The dosage of producer cells to be implanted will, of course, depend on precise circumstances of each patient, but typically the total number of implanted cells would be in the range from $10^4$ to $10^{12}$ per patient. The number of producer cells within each alginate or other encapsulating matrix will, of course, depend on the dimensions of the bead or other encapsulating form. The encapsulated producer cells will generally be surgically placed at the wound site following removal of the primary tumour.

As the experiments to be described in detail below have shown, encapsulated producer cells can survive, proliferate and maintain their specific expression periods in vitro and in vivo. This discovery opens up the possibility of a new kind of therapeutic treatment for patients with brain tumour conditions whereby different producer cells may be encapsulated which are chosen so as to target selected characteristics of brain tumour growth and development. In the experiments described herein, we have shown that specific MAbs released from alginate beads can inhibit tumour cell migration as demonstrated by an interference with epidermal growth factor receptor. We have also shown that specific products released from encapsulated producer cells within the brain penetrate into the brain parenchyma and can be distributed along CSF pathways.

The following experiments will assist in understanding the invention and its advantages. Hereafter reference will be made to the accompanying drawings, in which:

FIGS. 1A–1C

Light microscopic images of NIH 3T3 cells encapsulated in alginate. All bars represent 250 µm.

FIG. 1A: The day of encapsulation.

FIG. 1B: Encapsulated cells after 3 weeks in culture.

FIG. 1C: Encapsulated cells after 9 weeks in culture.

FIGS. 1D–1F: Scanning confocal laser micrographs of NIH 3T3 cells encapsulated in alginate. Viable cells emit green fluorescence (here shown as lighter areas), while dead cells emit red fluorescence (not here visible). All bars represent 250 µm.

FIG. 1D: At the day of encapsulation.

FIG. 1E: Encapsulated cells after 3 weeks in culture.

FIG. 1F: Encapsulated cells after 9 weeks in culture.

FIG. 1G: β-Galactosidase activity of BT4CnVlacZ cells encapsulated in alginate, after 9 weeks in culture. Bar represents 500 µm.

FIGS. 2A–2D

Flow cytometric histograms of NIH 3T3 cells encapsulated in alginate beads. The horizontal axis expresses the number of channels on the flow cytometer (relative DNA fluorescence), while the vertical axis expresses the relative number of cell nuclei in each channel.

FIG. 2A: Control, monolayer culture.

FIG. 2B: Cells encapsulated for 1 week.

FIG. 2C: Cells encapsulated for 3 weeks.

FIG. 2D Cells encapsulated for 9 weeks.

FIG. 3

Antibody release from H528 hybridoma cells encapsulated in alginate (mean value± standard error). The horizontal axis represents the number of days in culture, while the vertical axis shows the antibody release into the growth medium. The curve was estimated by a 3rd order regression analysis.

FIG. 4

Migration of cells from GaMg spheroids after 4 days, untreated (control), stimulated with 10 ng/ml EGF (EGF), or stimulated with 10 ng/ml EGF in the presence of encapsulated hybridoma cells (EGF/H528).

FIGS. 5A–5H

Encapsulated H528 hybridoma cells implanted into the rat brain.

FIG. 5A: Axial section of the rat brain. H&E-staining, bar represents 5 mm.

FIG. 5B: Same section as FIG. 5, showing encapsulated H528 cells inside the implantation site. H&E-staining, bar represents 500 µm.

FIGS. 5C–5H: Confocal laser scanning micrographs of the release and dissemination of monoclonal antibodies within the brain. FIGS. 5C, E and F were taken with identical gain settings. FIGS. 5G and 5H were also taken with identical gain settings.

FIG. 5C: A section of the brain parenchyma, with the encapsulated H528 cells at the far left side. Bar represents 150 µm. An intense fluorescence in the brain parenchyma is seen at the left side, followed by a gradual decrease in intensity at least 1000 µm into the brain.

The gradual change in fluorescence intensity along the horizontal line is further shown in FIG. 5D where the vertical axis represents the relative fluorescence intensity (0–255). An intense fluorescence is seen from the left side, with a gradual decrease into the brain parenchyma.

FIG. 5E: The MAbs were found in the subarachnoidal space and in the underlying brain. Bar represents 75 µm.

FIG. 5F: The weak fluorescence presented in the controls was probably caused by unspecific binding. Bar represents 75 µm.

FIG. 5G: MAbs were further spread within the perivascular space. Bar represents 50 µm.

FIG. 5H: In comparison, the controls showed a weak binding of immunoglobulins in the perivascular space. Bar represents 50 µm.

Experiments

Materials and Methods

1. Cell Lines

In our experiments, four different cell lines were used:

| Cell Line | Deposit Details |
|---|---|
| 1. NIH 3T3 | ATCC CRL/1658 |
| 2. BT4CnVlacZ | Not deposited |
| 3. H528ATCC | HB 8509 |
| 4. GaMg | Not deposited |

The mouse fibroblast NIH 3T3 cells represents a potential producer cell line in that it is capable of being genetically engineered to express substances which show effects against tumour growth, progression and development. The NIH 3T3 cells were encapsulated in alginate, as described below and used to study in vitro morphology, viability and cell kinetics. For studies of the viability of encapsulated cells in vivo, alginate beads containing NIH 3T3 cells were also implanted into the rat brain.

The BT4CnVlacZ cell line was originally developed from an ethylnitrosourea induced rat glioma and stably transfected with the bacterial lacZ gene, cloned into a plasmid containing a Moloney murine leukaemia virus long terminal repeat cassette with a neomycin resistance gene expressed from an internal Rous sarcoma virus promoter. See J. Natl Cancer Inst, 55 (1975), pages 1177–87 and Int. J. Cancer, 71 (1997), pages 874–80. The cells were encapsulated in alginate, and the in vitro synthesis of the bacterial β-galactosidase was studied.

The H528 hybridoma cell line was obtained from American Type Culture Collection (ATCC Rockville, Mass.). The cell line was generated by fusing NS-1-Ag4-1 myeloma cells with spleen cells from BALB/c mice, and it produces a mouse monoclonal antibody (MAb) (IgG2a) that binds to 1 and blocks the EGF-binding domain of the human epidermal growth factor receptor (EGFR). The in vitro and in vivo MAbs release from the alginate encapsulated cells was studied using this cell line.

The human glioma cell line GaMg has been described in Anticancer Res, 8 (1988) pages 874–80, and has previously been shown to express the EGFR (Acta Neuropathol Berl, 84 (1992), pages 190–197. The specific inhibition of GaMg cell migration was studied in a co-culture system between CaMg multicellular spheroids and encapsulated H528 cells.

2. Cell Culture

The NIH 3T3 and the BT4CnVlacZ cell lines were grown in 80 $cm^2$ culture flasks (Nunc, Roskilde, Denmark) with complete growth medium consisting of Dulbecco's modified Eagles medium (DMEM) supplemented with 10% heat inactivated newborn calf serum, four times the prescribed concentration of non-essential amino acids, 2% L-Glutamine, penicillin (100 IU/ml) and streptomycin (100 µg/ml) (all biochemicals from BioWhittaker, Verviers, Belgium). The H528 hybridoma and the GaMg cell lines were grown in 80 $cm^2$ culture flasks (Nunc) in RPMI 1640 growth medium supplemented with 10% horse serum (BioWhittaker). GaMg monolayers were trypsinized at confluence with 3 ml of 0.025% trypsin (BioWhittaker), and spheroids were initiated by seeding $5*10^6$ cells in 20 ml of complete RPMI medium into 80 $cm^2$ culture flasks (Nunc) base-coated with 0.5% agar noble (Difco, Detroit, Mich.) (30) in complete RPMI medium. All cell lines were kept in a standard tissue culture incubator at 37° C., with 100% relative humidity, 95% air and 5% $CO_2$.

3. Structure and Properties of Alginate

In these experiments sodium alginate from the brown seaweed Laminaria hyperborea (LF 10/60) (Protanal, Drammen, Norway) was used for microencapsulation of the producer cells. This consists of two monosaccharides; α-L-guluronic acid (G) and β-D-mannuronic acid (M). The G- and M-units are joined together in three different types of blocks, GG, MM and MG, and the proportions and distributions of these blocks determine the chemical and physical properties of the alginate molecules. Some divalent cations like $CA^{2+}$ bind strongly between separate G-blocks, which initiate the formation of an extended alginate network where the G-blocks form stiff junctions. The alginate which we used has a high content, above 60%, of G-blocks, resulting in high mechanical stability and porosity, rendering it suitable for encapsulating cells for production of secondary metabolites (see Trends in Biotechnology, 8 (1990), pages 71–78). Scanning electron microscopy has showed pore sizes in the alginate beads to range between 5 and 200 nm (33,34). Mechanical strength, volume stability and porosity of the beads correlate to the content of guluronic acid.

4. Encapsulation of Cells

The method of encapsulation used has been described in detail in "Alginate as Immobilization Matrix for Cells" by Smidsrød and Skjak-Braek in Trends in Biotechnology, March 1990, Vol. 8, No. 3, pages 71–78.

Briefly, droplets of cells dispersed in 1.5% sodium alginate were released into a 0.1M $Ca^{2+}$-solution. After polymerization, the alginate beads were washed three times in Dulbeccols PBS (DPBS; Sigma, St. Louis, Mo.), and once in growth medium. The encapsulated cells were cultured in 175 $cm^2$ culture bottles (Nunc), containing 50 ml growth medium. The growth medium was changed every third day, and the bottles were replaced once a week. All alginate encapsulated cells were kept in a standard tissue culture incubator at 37° C., with 100% humidity, 95% air and 5% $CO_2$. For all the experiments with the NIH 3T3 and the BT4CnVlacZ cell lines, a cell density of $6*10^4$ cells/ml alginate and bead sizes between 0.8 and 1.2 mm were used. For the in vitro experiments with the H528 cell line a cell density of $3*10^5$ cells/ml alginate and bead diameters between 2.3 and 2.5 mm were used. For the in vivo experiments with the H528 cell line, a cell density of $3*10^5$ cells/ml alginate and bead diameters between 0.8 and 1.2 mm were used.

In Vitro Experiments

1. Morphology and Viability of Alginate Encapsulated Cells

The morphology of NIH 3T3 cells encapsulated in alginate was investigated at the day of encapsulation, and after 3 and 9 weeks, in 6 beads transferred to a 6-well dish (Nunc) with an overlay of 1.0 ml DPBS. The beads were examined with a Nikon Diaphot light microscope, and photographed with a Nikon F-301 camera. The morphology experiments were performed in duplicate.

The viability of the cells within the alginate beads was investigated at the day of encapsulation, and after 3 and 9 weeks, by a two-colour fluorescence viability assay (Live/Dead™ viability/Cytotoxity Assay, Molecular Probes, Eugene, Oreg.). A labelling solution was prepared with 2 $\mu M$ calcein-AM and 4 $\mu M$ ethidium homodimer in complete growth medium. The alginate beads were individually placed in 16-mm multiwell dishes (Nunc) with an overlay of 0.5 ml labelling solution of 30 minutes at room temperature. Thereafter they were transferred into DPBS and examined immediately. The fluorescence was measured in optical sections through the alginate using a confocal laser scanning microscope with an argon-krypton laser (Biorad MRC-1000, Hemel Hempstead, England), using Texas Red and FITC filter optics. Fluorescence was recorded in a plane 120 $\mu m$ inside the alginate beads. The viability experiments were performed in triplicate.

The production of β-galactosidase in BT4CnVlacZ cells encapsulated in alginate for 1, 3 and 9 weeks was studied. The beads were washed for 1 minute in DPBS (pH=8.4), and fixed for 10 minutes in 0.2% glutaraldehyde and 2% formaldehyde in DPBS. Thereafter they were washed 3×5 minutes in DPBS and stained for β-galactosidase activity with 5-bromo-4-chloro-3-indolyl β-D-galacto-pyranoside (x-gal; Sigma). The substrate solution consisted of 1 mg/ml x-gal dissolved in 100 $\mu l$ dimethylformamide, and mixed with 5 mM potassiumferricyanite, 5 mM potassiumferrocyanate and 2 mM $MgCl_2$ dissolved in DPBS (all biochemicals from E. Merck, Darmstadt, Germany). They were incubated at 4° C. for minimum 24 hours, and examined for β-galactosidase activity, represented by a blue coloured cell cytoplasm.

2. Cell Kinetics of Alginate Encapsulated Cells

The in vitro cell cycle distribution of the encapsulated NIH 3T3 cells was determined by flow cytometric DNA analysis. The encapsulated cells were released from the alginate by dissolving the beads in complete growth medium containing 1.5% tri-sodium citrate dihydrate (E. Merck) for 15 minutes, followed by centrifugation at 140 g for 4 minutes, and removal of the supernatant. The cells were re-suspended twice in complete growth medium, centrifuged at 140 g for 4 minutes, fixed in ice cold 96% ethanol and stored at 4° C. Prior to the flow cytometric analysis, the cells were incubated for 15 minutes with 0.5% pepsin (Sigma) in 0.9% physiological saline (pH=1.5) at 37° C. before the isolated nuclei were washed in 0.9% physiological saline, and treated for 1 minute with ribonuclease (Sigma) (1 mg/ml in 0.9% physiological saline). Staining of DNA was obtained by adding propidium-iodide (Sigma) (50 $\mu g/ml$ in 0.9% physiological saline) to the nuclei. The cellular DNA content was measured using a Becton Dickinson FACSort flow cytometer (Becton Dickinson, Palo Alto, Calif.). The DNA histograms were obtained by gating a two parameter forward- and side-scatter cytogram to a one parameter DNA histogram. Each histogram was obtained by counting a total of 5000 gated nuclei. The flow-cytometric experiments were repeated three times, and the cell cycle distribution was determined as described in Radiat Environ Biophys, 12 (1975), pages 31–39.

3. Antibody Release from the Encapsulated Hybridoma Cells

Alginate beads with diameters between 2.3 and 2.5 mm containing $1.5*10^3$ H528 cells per bead on the day of encapsulation were prepared as described above. After 0, 1, 5, 12, 19, 23, 30 and 33 days, respectively, 10 beads were removed from the stock culture and the release of Mabs into the RPMI medium was examined. The beads were transferred into 24 well dishes (Nunc), in 0.5 ml complete RPMI medium (37° C.). After 6 hours of incubation, four samples of 100 $\mu l$ each were collected, placed in 1.5 ml centrifuge test tubes (Treff AG, Degersheim, Switzerland) and frozen at −20° C.).

Flow cytometry was used to determine the concentration of MAbs in the samples. GaMg monolayer cell cultures were typsinized with 2 mM EDTA in DPBS. The cells were then centrifuged at 140 g for 4 minutes, the supernatant was removed, and the cells were fixed in 2% paraformaldehyde solution in DPBS for 1 minute. Thereafter the cells were centrifuged at 140 g for 4 minutes, and the supernatant was removed. The cells were then re-suspended in DPBS containing 2 mM EDTA, 1% bovine serum albumine and 1 g/l glucose, and distributed in a conical 96 well plate (Nunc) with $1.7*10^5$ cells/well. The cells were centrifuged at 340 g for 4 minutes, and the supernatant was removed. Thereafter the cells were vortexed and incubated for 2 hours at 4° C. with the harvested MAb RPMI medium (undiluted, and 1:5, 1:20 and 1:100 dilutions in DPBS). As a reference, an EGFR MAb (528) antibody (Santa Cruz Biotechnology, Santa Cruz, Calif.) with a known MAb concentration was used (concentrations 20, 5, 1, 0.2, 0.1 and 0.05 $\mu g/ml$). The cells were washed twice in 2 mM EDTA, 1% BSA, 1 g/l glucose in DPBS, and then incubated with FITC-conjugated goat anti-mouse immunoglobulins (Dako A/S, Glostrup, Denmark) (1:20 dilution) for 30 minutes at 4° C. Flow cytometry was performed on a Becton Dickinson FACSort flow cytometer. Single cells were detected and visualized by a two parameter forward- and side-scatter cytogram and gated to a one parameter FITC histogram, where the fluorescence intensity was determined. By using the various titers of the EGFR MAb with a known concentration on the GaMg cells, a reference antibody binding curve to GaMg cells was obtained. By comparing the results obtained from medium harvested from the hybridoma containing alginate beads, the MAb concentration curve was obtained.

4. Cell Migration

Gamg spheroids were individually transferred to 16-mm multiwell dishes (Nunc), in 1.0 ml complete RPMI medium containing 10 ng/ml EGF (Sigma). Thereafter, the tumour cells were exposed to alginate beads containing H528 cells (three alginate beads in each well). As controls, spheroids were exposed to complete RPMI medium with or without 10 ng/ml EGF. The orthogonal diameter of each colony was measured daily for four days, using a light microscope with a calibrated reticle in the ocular. The circular area covered by the cells migrating out from the spheroids was then determined and used as an index of cell migration. The experiments were performed in duplicate, with six spheroids in each experiment.

5. Establishment of Endostatin Producer Cells and Proof: The Endostatin Release from the Beads 5A. Establishment of Endostatin Producer Cells Methods: Cell Line and Culture Conditions.

Human foetal kidney 293 cells (293-EBNA) expressing the Epstein-Barr virus nuclear antigen (EBNA)-1 were used as a producer cell line.

The cells were transfected with the episomal expression vector pCEP-Pu containing the gene encoding human endostatin, by liposomal and selected with 0.5 $\mu$g/ml puromycin.

The transfected cells (293-endo) were grown to confluency in 175 cm2-culture flasks (Nunc, Roskilde, Denmark) containing growth medium consisting of Dulbecco's modified Eagles medium (DMEM) supplemented with 10% heat-inactivated foetal calf serum, 4.5 g/l D-glucose, penicillin (100 IU/ml) and streptomycin (100 $\mu$l/ml), 205 $\mu$g/ml geneticin. (G-418) and 0.5 $\mu$g/ml puromycin. Mock transfectants were generated by transfecting 293 cells with the pCEP-Pu vector without the endostatin gene and grown under the same conditions with the exception of puromycin (all Biochemical products from Biowhitaker, Verviers, Belgium).

The tumour cell line (BT4C) chosen for these experiments was developed from an ethylnitrosourea induced rat gliosarcoma (passage number 26) and is syngeneic in BD-IX. The cells were grown to confluency in 80 cm2 culture flasks with complete growth medium consisting of Dulbecco's modified Eagles medium (DMEM) supplemented with 10% heat-inactivated new-born calf serum, 4 times the prescribed concentration of non-essential amino acids, 2% L-Glutamin, penicillin (100 IU/ml) and streptomycin (100 $\mu$l/ml).

5b. Estimation of Endostatin Release from the Beads. Immunoblots.

Conditioned medium from encapsulated endo-293 and 293-EBNA was collected and used for standard SDS/PAGE Western blotting to determine whether endostatin was released from the beads.

Briefly, the samples were separated on a 12% SDS gel and blotted onto a PVDP nitrocellulose membrane. The blots were washed with 100% methanol for 5 min, dest. water 1 min, blocking solution (0.05 M Tris/HCL, 0.45 M Nacl, 2% Tween, ph 10.2) 4 min and finally with washing buffer (0.05 M Tris/HCL, 0.15 M Nacl, 0.05% Tween 20, ph 10.2.) for 15 min. The blots were then incubated over night with Rabbit anti-human anti-sera (1:1000 in wash buffer). Following over night incubation, the blots were washed in DPBS and incubated with pig anti-rabbit alcaline phosphatase conjugated IgG (DAKO, Denmark). Visualisation of the bands was performed by incubation with of the substrate staining solution (2–4 min).

In Vivo Experiments

1. Intracranial Implantations

Male inbred BD-IX rats (36) weighing between 160 g and 250 g were kept on a standard pellet diet, given unlimited access to tap water and caged individually at a constant temperature and humidity on a 12 hour light and dark schedule. The rats were anaesthetized intraperitoneally with pentobarbitol at a concentration of 0.4 ml/100 g body weight. Via a mid-sagittal skin incision, a burrhole was made with a 3.5 mm drill 4.2 mm posterior to the bregma point and 2.5 mm to the right of the sagittal suture. Cortical and white matter tissue was removed by suction to a depth of 2.0 mm, and between 8 and 14 alginate beads (one day old beads) containing either NIH 3T3 cells or H528 cells were placed in the tissue cavity. The burrhole was closed with bone wax and the skin sutured with polyamide thread. Recovery under a heating lamp was allowed for 1 hour. The animal care was in accordance with institutional guidelines. The rats were observed once a day, and weighed every other day. All animals recovered quickly after the implantations, and did not show any signs of illnesses or neurological deficits during the observation period.

2. Release and Dissemination of Immunoglobulins within the Rat Brain

After 3 and 9 weeks, the rats were sacrificed by $CO_2$ inhalation. The brains were removed, embedded in Tissue Tek (Miles Laboratories Inc., Naperville, Ill.) and frozen in 2-Methylbutane (E. Merck) cooled with liquid nitrogen. Axial sections (14 $\mu$m) were cut on a Reichert-Jung, cryocut 1800 cryotome (Leica, Wetzlar, Germany), and stored at −20° C. Cryosections obtained from rats implanted with H528 encapsulated cells and sacrificed after 3 weeks, were fixed in acetone for 5 minutes at room temperature, and then washed twice in DPBS for 5 minutes. The sections were then incubated with FITC-conjugated goat anti-mouse immunoglobulins (Dako A/S; 1:20 dilution) for 1 hour at room temperature, and thereafter washed for 5 minutes with DPBS. The sections were treated for 30 seconds with ribonuclease (Sigma) (0.5 mg/ml in 0.9% physiological saline), and staining of the nuclei was obtained by adding propidium-iodide (Sigma) (50 $\mu$g/ml in 0.9% physiological saline) to the sections. Furthermore, the sections were washed with DPBS for 5 minutes, and then mounted with Vectashield (Vector Laboratories Inc, Burlingame, Calif.). The fluorescence was measured using a Leica TCS NT confocal laser scanning microscope with an argon-krypton laser (Leica), using TRITC and FITC filter optics. Sections taken from the same depth within the brains of the experimental animals were investigated, and the areas of maximum fluorescence intensity were studied in both groups. Cryosections obtained from rats implanted with NIH 3T3 cells and sacrificed after 9 weeks, were stained with Haematoxylin nd Eosin for histological examination.

3. Immune Responses Towards Producer Cells Encapsulated in Alginate.

Methods

The percentage of immuno-positive cells at the border zone between brain to BD-IX rats and alginate beads was evaluated 1,3 and 9 weeks after implantation. The brains were mounted on stubs, embedded in tissue-tek and frozen in liquid N2. Serial axial sections 5–10 $\mu$m were cut on a Reichert Jung Cryostat (Leica, Wetzlar, Germany) mounted on slides and prepared for immunohistochemical analyses. Sections were fixed in cold acetone for 5 min, incubated for 30 min. at room temperature with 10% normal rabbit Serum, diluted in PBS, and thereafter incubated over-night at 4° C. in a humidity chamber with mouse monoclonal antibodies (mAbs) diluted in 10% rabbit serum. The following mAbs were used: OX42, ED1, and ED2 anti-rat macrophage mAbs, OX19 against CD5 positive T cells, and OX33 reactive with CD45RA positive B cells. The mAbs were obtained from Serotec, Oxford, UK.

Biotinylated rabbit anti-mouse immunoglobulins diluted 1:300 were applied for 30 min. Avidin-biotin-peroxidase complex (ABCcomplex/HRP, Dakopatts, Glostrup, Denmark) was prepared as recommended by the manufacturer, and allowed to react with the sections for 30 min. Finally, the sections were treated with a buffer containing 3-amino-9-ethyl-carbazole, for the development of a coloured reaction product. Washing in PBS followed all incubations. All preparations were counterstained with hematoxylin, mounted in Glycergel (Dakopatts,), and analysed by light microscopy.

4. Effects of Endostatin Alginate-Therapy on Tumour Growth

Young adult BD-IX rats of both sexes (8 rats in total, plus 20 controls) were anaesthetised by intraperitoneal injections of Equithesine at a dosage of 0.4 ml/100 g body weight. The rats were immobilised in a stereotactic frame (David Kopf Instruments, Tujunga, USA), the skin was incised and a 2 mm burr hole was made 1 mm posterior to and 3.0 mm to the right of the Bregma point, and inserted to a depth of 2.5 mm. Using a injected in to the brain. Following this 1×104 BT4C gliosarcoma cells were injected 1 mm lateral to the alginate beads at a depth of 2 mm. The alginate beads contained either endostatin producing 293 cells or 293-mock transfectants, as controls. Eight animals received implants form each cell line. Furthermore, as a control of normal tumour progression, 8 animals were injected with BT4C cells alone.

Finally, as a control of the in vivo viability of the cells within the beads, the remaining 4 control animals received alginate beads containing 293-endo cells alone. The syringe was slowly retracted over 3 min (for all injections) and closure was performed with bone wax and suture. The animals were allowed to recover from surgery under observation. During the experimental period the animals were housed in pairs at constant temperature and humidity, fed a standard pellet diet and provided tap water at libitum.

Results

In Vitro Experiments

1. Morphology and Viability of the Alginate Encapsulated Cells

Figure 1:
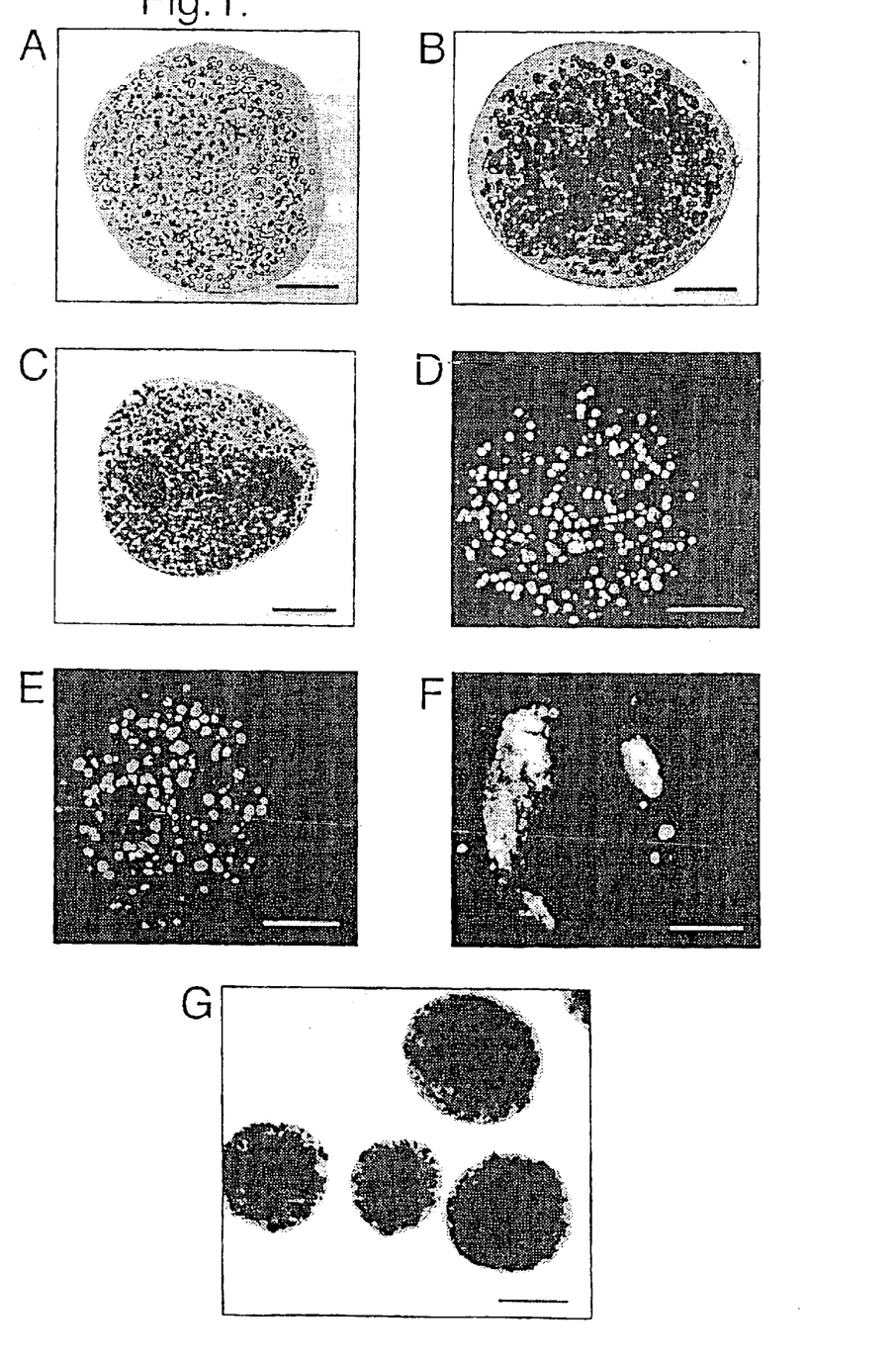

Alginate beads with diameters of 1.0 mm contained approximately $6.5*10^2$ NIH 3T3 cells on the day of encapsulation (FIG. 1A). The cells were evenly distributed within the alginate beads, with an outer cell free rim of 25–50 µm. During culture, cell proliferation was observed within the alginate, resulting in an increased cellular density after 3 weeks (FIG. 1B). After 9 weeks in culture, multicellular spheroids were observed within the alginate beads (FIG. 1C). Over 90% of the beads remained intact after 9 weeks in culture, as assessed by light microscopy. After about a week in culture a few single cells migrated out from the alginate beads and into the growth medium, and this limited movement of single cells continued during the next 8 weeks of culture.

The confocal laser scanning microscopy study showed that around 90% of the encapsulated cells remained viable on the day of encapsulation (FIG. 1D). After 3 weeks in culture, around 50% of the originally encapsulated cells were viable (FIG. 1E). Some of the surviving cells adapted to the alginate and formed viable multicellular spheroids, which could be clearly observed after 9 weeks (FIG. 1F). At this time point the total number of viable cells within the beads were difficult to assess due to the multicellular spheroid formation. However, as shown in FIG. 1F, most of the cells localized in the spheroids were viable.

The encapsulated BT4CnVlacZ cells expressed a constant and evenly distributed β-galactosidase activity during the whole observation period of 9 weeks (FIG. 1G).

2. Cell Kinetics of Alginate Encapsulated Cells

Figure 2:
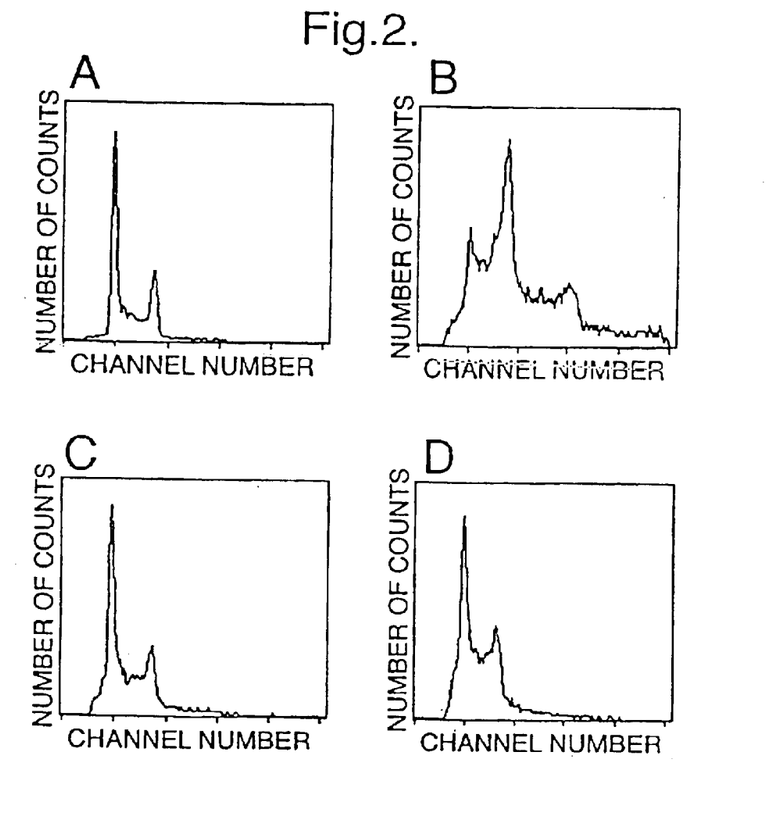

The flow cytometric histograms of the NIH 3T3 cells showed a change in cellular ploidy within the alginate beads 1 week after encapsulation (FIG. 2B). This probably represents a polyploidization, as compared to the diploid control (FIG. 2A). However, after 3 and 9 weeks respectively (FIGS. 2C, 2D) a normalization in ploidy was observed, with a similar diploid distribution as for the controls. The fraction of proliferating cells in the S and $G_2M$ phases was 50% for the control, as compared to 55% and 60% after 3 and 9 weeks in vitro, respectively.

3. Antibody Release from the Encapsulated Hybridoma Cells

Figure 3:
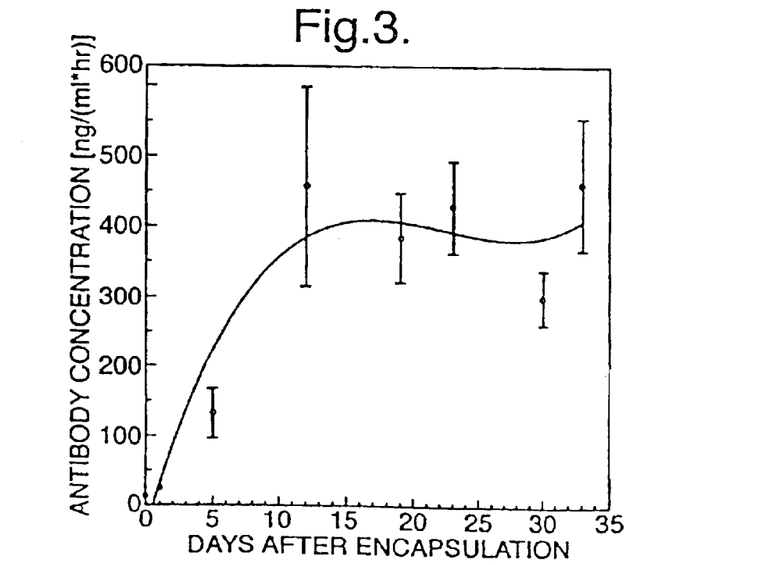

Already at the end of the first day of encapsulation, there was a release of 13 ng/(ml*hr) of MAbs in the growth medium (FIG. 3). The diffusion of immunoglobulins out of the beads and into the medium increased steadily during the next days of culture, and reached a concentration of 457 ng/(ml*hr) after 12 days. The production of MAbs then stabilized around 400 ng/(ml*hr) during the last 3 weeks of the observation period.

4. Cell Migration

Figure 4:
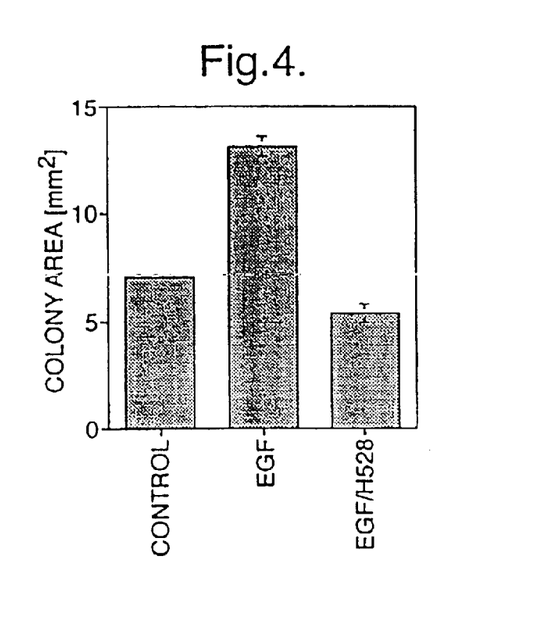

The migration of cells out from the GaMg spheroids stimulated with EGF was extensive, and the mean outgrowth area was doubled, compared to the controls (FIG. 4). However, when alginate beads containing H528 cells were added in the presence of EGF, cell migration was strongly inhibited, demonstrating that the encapsulated H528 producer cells effectively express an antibody directed against the EGF receptor.

5. Estimation of Endostatin Release from the Beads.

Figure 6:
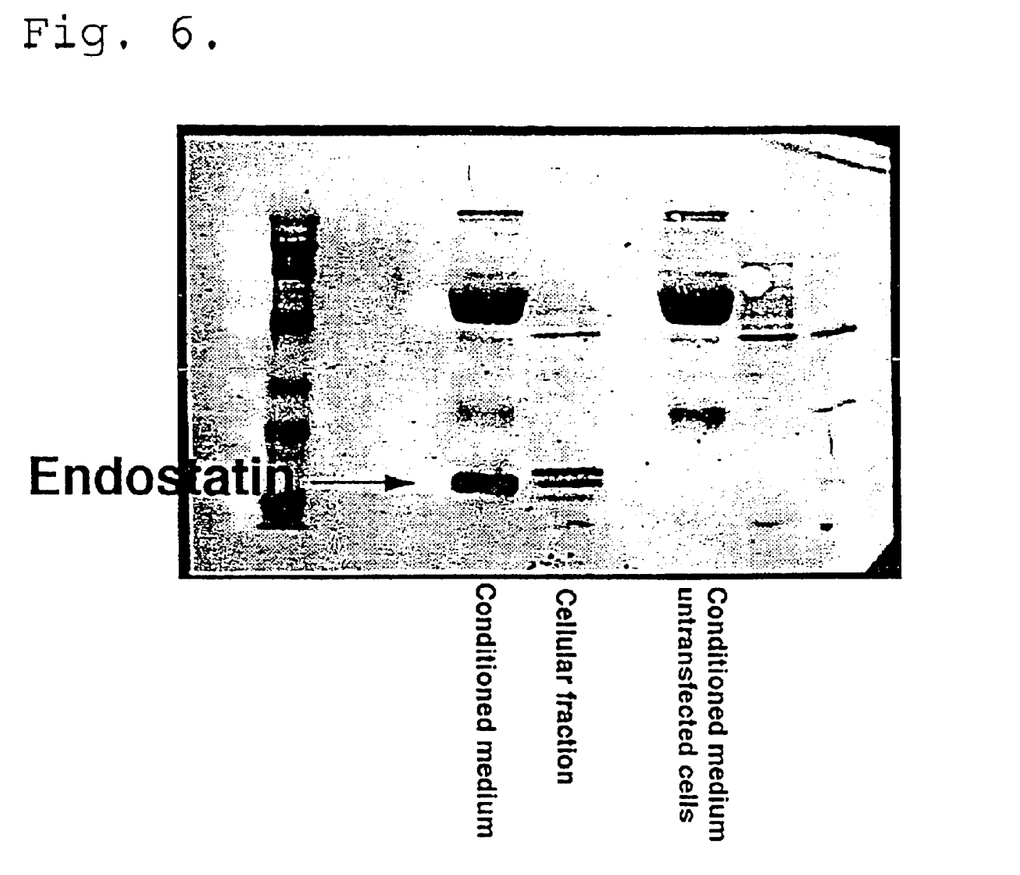
FIG. 6: Radioimmunoassays that shows the successful establishment of endostatin producer cells. The figure shows radioimmunoassays of endostatin release from conditioned medium, in cellular fractions and medium from untransfected cells in the second, third and the fourth column, respectively.

As seen from the western blots of conditioned medium harvested from the beads, a substantial amount of endostatin is released from the beads (FIG. 6). The radioimmunoassays have shown that 10 endostatin producing alginate beads (400 µm) with 25000 cells encapsulated, secreted 2.5 µg/ml/24 hrs.

In Vivo Experiments

1. Intracranial Implantations

Figure 5:
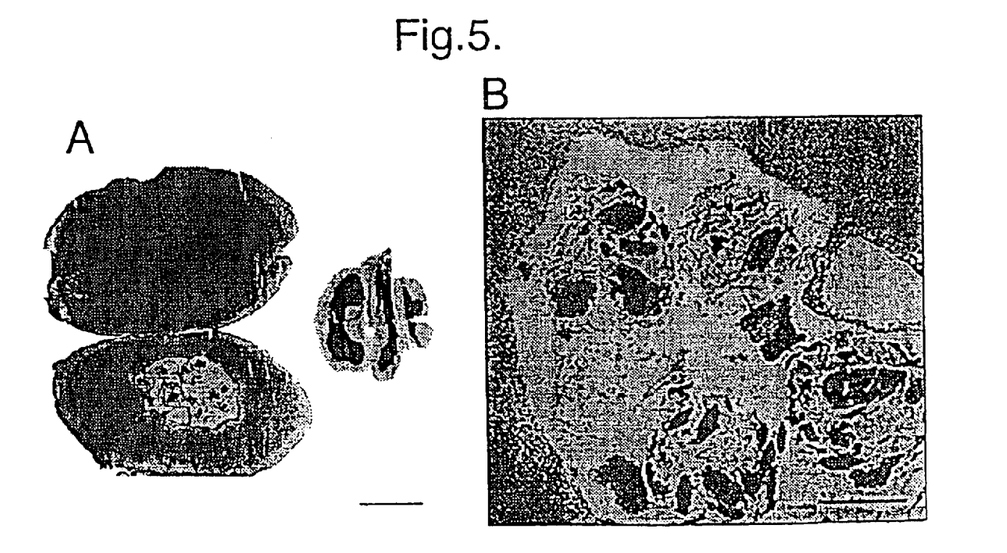

Axial sections of the rat brains revealed little or no change in the brain parenchyma adjacent to the implantation site harbouring the alginate encapsulated NIH 3T3 cells (FIG. 5A). Little intracranial edema or swelling was observed after 9 weeks. The alginate beads were free of any cell overgrowth, and contained both viable single cells and multicellular spheroids (FIG. 5B). The viable cells were distributed both in the centre and in the periphery of the beads, with cell-free areas of alginate in between the cells. A minimal aggregation of cells around the border zone between the implantation hole and the brain parenchyma was observed.

2. Release and Dissemination of Immunoglobulins Within the Rat Brain

The implanted beads with encapsulated hybridoma cells were easily visualized after 3 weeks by an intense green fluorescence (FIG. 5C). Immunoglobulins were detectable in the brain tissue at a distance of at least 1 mm from the alginate beads (FIGS. 5C, 5D), with a gradual decrease in fluorescence intensity from the border of the implantation site and into the brain. For two of the experimental animals, MAbs were detected in the whole cerebral hemisphere, where the implants were located (data not shown). MAbs were further found in the leptomeninges in both hemispheres of the cerebrum (FIG. 5E), with the strongest fluorescence seen in the subarachnoidal area in the right hemisphere. The negative controls showed a weak fluorescence in the leptomeninges, probably caused by non-specific binding between the immunoglobulins and epitopes on the leptomeningeal cells (FIG. 5F). However, the brain parenchyma was negative. The MAbs were further present in the perivascular space of intracerebral blood vessels, with no apparent difference in fluorescence intensity between the two hemispheres (FIG. 5G). The weak fluorescence present in the control was again probably caused by non-specific binding (FIG. 5H).

3. Immune Responses Towards Producer Cells Encapsulated in Alginate.

Infiltration of mononuclear cells was observed in the brain adjacent to the alginate beads. The amount of cells in the infiltrate decreased from week 1 to week 9. One week after implantation OX42 positive microglia with a dendritic morphology were seen in the parenchyma and reactive microglia and invading monocytes appeared at the border zone towards the alginate beads. ED1 and ED2 stained monocytes close to the border zone whereas few cells were stained by these mAbs elsewhere in the brain parenchyma. A limited number of T and B cells were also observed at the border zone to the beads (Table I). The amount of OX42 positive cells at the border zone decreased from 62% at week one to 20% at week 9, whereas the ED1 positive cells decreased from 34% at week one to 7% at week 9. The amount of ED2 positive cells (5%), T cells (14%), and B cells (1%) changed only marginally during the observation period (Table I).

TABLE I

Cellular immune response in rat brain tissue 9 weeks after implantation of NIH 3T3 cells in alginate

| Cells | Immunoreactivity |
| --- | --- |
| T cells (CD5) | No reactivity |
| B cells (CD45RA) | No reactivity |
| Microglia and macrophages (OX42) | High reactivity |
| Macrophages and monocytes (ED1/ED2) | Weak reactivity |

4. Effects of Endostatin Alginate-Therapy on Tumour Growth

Figure 7:
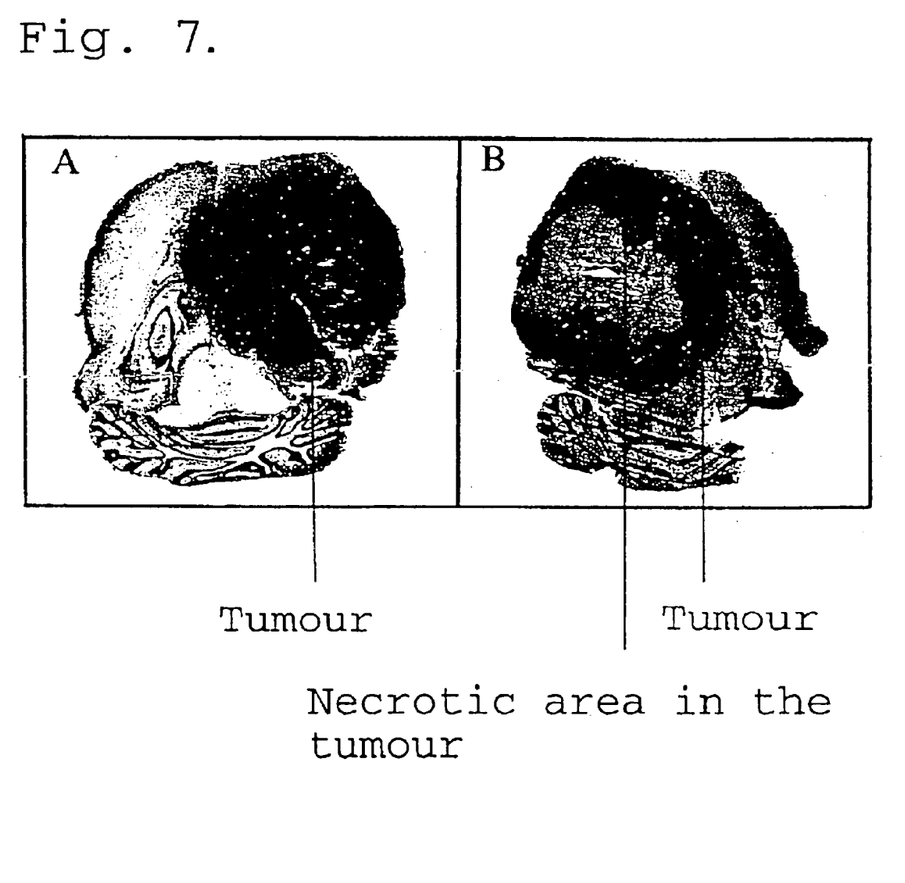
FIG. 7: Effects of endostatin alginate therapy on tumour growth. Panel A shows example of a control animal where mock transfected cells encapsulated in alginate beads were implanted. The darker area of the brain shows the tumour area. Panel B shows example of an animal treated with encapsulated endostatin producing cells. The darker area shows the tumour, and a large necrotic area is visualised in the middle of the tumour.

The animals treated with endostatin-producer cells in alginate lived 20%+/−4% longer than animals treated with mock transfected cells. Detailed histological observations revealed large necrotic areas in the tumours that received endostatin-alginate therapy (see. FIG. 7, panel B). Such necrotic areas were never seen in the controls (mock transfected cells encapsulated in alginate; FIG. 7, panel A).

Discussion

The results of the above-described experiments clearly demonstrate that the microencapsulated cells survive, proliferate and maintain their phenotypic expression over extended time periods. It is also shown that MAbs released from the alginate beads have the ability to inhibit tumour cell migration in vitro by interfering with the EGFR, and that MAbs are released and disseminated within the rat brain.

As seen by light microscopy, the NIH 3T3 cells adapted to the alginate in vitro, and started to proliferate within a few days after encapsulation. The CLSM study revealed cell viability around 90% at the day of encapsulation. During the first three weeks in culture, around 50% of the initially entrapped cells died within the beads. However, after 9 weeks, the remaining cells showed the ability to form multicellular spheroids within the alginate. An observed cell death within the alginate has also been reported by others, and may be due to a reduced diffusion of oxygen, nutrients and waste products, which may eventually lead to an equilibrium between the number of proliferating and dying cells. A more favourable diffusion rate may be achieved by decreasing bead size, increasing the content of G-units, which would increase the pore sizes, or changing the alginate concentration. In addition, the diffusion is dependent on the number of initially encapsulated cells within the beads. The alginate itself is non-toxic, and can therefore not be expected to contribute to the observed cell death within the beads.

The BT4CnVlacZ cells exhibited a strong and evenly distributed β-galactosidase activity during 9 weeks of culture. These results demonstrate that also specific gene products may be produced during prolonged periods within alginate beads.

The flow cytometric study showed that the NIH 3T3 cells changed from a diploid to a multiploid population after 1 week in alginate. This indicates that the cell nuclei divide, but because of limited space within the rigid alginate network, the cells are initially not able to undergo cytokinesis. This will then result in single cells with double and triple nuclei (FIG. 2B). However after 3 weeks, the cell cycle distribution was similar to the controls. This may indicate that the cells need a certain adaptation period within the alginate, were single cells with double and triple nuclei will either finish their cytokinesis or die. The histograms after 9 weeks were similar to those after 3 weeks, but indicated an increase of cells in the proliferating phases. The analysis of the cell cycle distribution showed an increase in the number of proliferating cells, from 50% for the control, to about 60% after 9 weeks. This may be due to a selection within the alginate beads of cells with a higher proliferative capacity during prolonged culture of the NIH 3T3 cells.

The antibody release from the encapsulated H528 hybridoma cells was substantially constant at around 400 ng/ml*hr from day 12 to day 33, which shows that a stable density of MAb-secreting hybridoma cells had been established after 12 days in culture. This finding is important for the clinical situation, as it shows stable monoclonal antibody production is achieved at a high level.

The cell migration out from the GaMg spheroids was stimulated in the presence of EGF. By adding H528 encapsulated cells to the EGF stimulated spheroids, the migration was inhibited, and the outgrowth area was similar to the controls. This implies that paracrine cell proliferation mechanisms are inhibited by these Mabs, probably by blocking the EGF-binding domain of the EGFR.

Implantation of alginate-encapsulated producer cells in other organs outside the central nervous system (CNS) has shown a fibroblast overgrowth of the alginate beads, leading to cell death and graft failure (Transplantation, 54 (1992), pages 769–774). Due to the unique location, and the lack of fibroblasts in the CNS, the same cell overgrowth was not observed in the present study (FIGS. 5A, B). Depending on the composition, alginates have in some instances been shown to trigger an immune response within the body by stimulating monocytes to produce high levels of cytokines. The cytokine-stimulating part of the alginate are the M-units. An alginate with a high content of G-units was therefore chosen for our experiments, in order to minimize the immune response within the brain. In further experiments we have found a low immune response towards alginate encapsulated cells within the brain, with only some microglial cells assembling in the brain tissue close to the implanted beads. These observations further show alginate-encapsulated producer cells to be an attractive treatment within the brain. A minimal aggregation of cells around the border zone between the implantation site and the brain parenchyma was also seen. This may be due to NIH 3T3 cells escaping from the alginate beads, because of a mild immune response towards the implants as discussed above, and/or due to a tissue wound-healing process. It is, however, not considered that the small number of producer cells which escape the alginate represents a problem, since these cells would be taken care of by normal graft versus host rejection mechanisms. However, if desired, steps can be taken to prevent cell escape eg by covering the beads with a layer of poly-L-lysine or by irradiating the cells prior to encapsulation, thereby inhibiting their proliferative capacity. The immunoglobulins were released from the alginate beads, and disseminated into the brain parenchyma at a distance of at least 1 mm away from the border of the implantation site. In two of the experimental animals, MAbs were also detected in the whole cerebral hemisphere where the implants were located. This dissemination may be due to a passive diffusion process. MAbs were also localized in the subarachnoidal area and within the perivascular space of Virchov-Robin. This spread is most likely mediated by the constant flow of cerebrospinal fluid within the CNS. Interestingly, tumour cells follow the same dissemination pathways within the brain, which make them accessible to components produced by alginate encapsulated cells.

In summary, the experiments which are described above show that encapsulated producer cells survive and proliferate within the alginate for prolonged time periods, in vitro as well as in vivo. Gene products such as β-galactosidase are produced within the cell cytoplasm of the encapsulated BT4CnVlacZ cells during several weeks of culture. Encapsulated hybridoma cells further produce and release high amounts of MAbs in vitro and in vivo. The GaMg tumour cell migration is inhibited in the presence of encapsulated H528 cells. Implants of encapsulated H528 cells also produce and release MAbs within the rat brain, and the MAbs disseminate within the brain parenchyma, as well as within the subarachnoidal and in the perivascular space. The present invention therefore represents a promising tool for CNS tumour therapy.

What is claimed is:

1. A composition comprising a producer cell that expresses a molecule that is an inhibitor of the growth of a CNS tumor, the cell being encapsulated in a matrix that comprises an immunoisolating alginate having a G content of above 15%, wherein the molecule is endostatin, angiostatin, thrombospondin, or prolactin; the producer cell is encapsulated in a bead or microbead; and the alginate concentration within the bead or microbead increases from the center of the bead or the microbead to the outer rim.

2. The composition according to claim 1, wherein the alginate has a G content of above 50%.

3. The composition according to claim 1, wherein the alginate has a G content of 60%–80%.

4. The composition according to claim 1, wherein the alginate has a G content of 80%–100%.

5. The composition according to claim 1, wherein the cell's expression of endostatin, angiostatin, thrombospondin, or prolactin is switched on and off by an external pharmacological agent.

6. The composition of claim 1, wherein the CNS tumor is a brain tumor.

7. The composition according to claim 1, wherein the alginate is substantially free of endotoxin.

8. A method of producing the composition according to claim 1, comprising introducing, in a drop-wise manner, a mixture of the producer cells that express a molecule that is endostatin, angiostatin, thrombospondin, or prolactin and the alginate into a solution containing multivalent cations.

9. A method of producing the composition according to claim 1, comprising the step of adding, in a drop-wise manner, an alginate solution containing at least one viable cell that expresses a molecule that is endostatin, angiostatin, thrombospondin, or prolactin to a calcium-containing solution.

10. A pharmaceutical composition comprising (a) the composition according to claim 1 and (b) a pharmaceutically acceptable carrier or diluent.

11. A method of treating a mammalian patient afflicted with a CNS tumor comprising the step of administering to the patient an effective amount of the pharmaceutical composition according to claim 10.

12. The method of treatment according to claim 11, wherein the CNS tumor is a brain tumor.

13. The composition according to claim 1 wherein the producer cell comprises a plasmid that includes a nucleic acid sequence that encodes endostatin, angiostatin, thrombospondin, or prolactin.

14. The method according to claim 8 wherein the solution containing multivalent cations is substantially free of sodium chloride.

15. The method according to claim 9 wherein the solution containing multivalent cations is substantially free of sodium chloride.

* * * * *